United States Patent
Kato (10) Patent No.: US 8,777,983 B2
(45) Date of Patent: Jul. 15, 2014

(54) DEFECT-CLOSURE DEVICE AND DELIVERY APPARATUS

(75) Inventor: Yukitoshi Kato, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 858 days.

(21) Appl. No.: 11/887,453

(22) PCT Filed: Mar. 28, 2006

(86) PCT No.: PCT/JP2006/306294
§ 371 (c)(1),
(2), (4) Date: Nov. 13, 2007

(87) PCT Pub. No.: WO2006/104147
PCT Pub. Date: Oct. 5, 2006

(65) Prior Publication Data
US 2009/0082804 A1    Mar. 26, 2009

(30) Foreign Application Priority Data

Mar. 29, 2005    (JP) .................................. 2005-094160

(51) Int. Cl.
*A61B 17/08* (2006.01)
*A61B 17/128* (2006.01)
*A61B 17/122* (2006.01)
*A61B 17/00* (2006.01)

(52) U.S. Cl.
CPC ... *A61B 17/1285* (2013.01); *A61B 2017/00615* (2013.01); *A61B 2017/00592* (2013.01); *A61B 2017/00597* (2013.01); *A61B 17/1227* (2013.01); *A61B 2017/00623* (2013.01); *A61B 17/0057* (2013.01); *A61B 2017/00575* (2013.01)

USPC .......................................................... 606/213
(58) Field of Classification Search
USPC ......................................... 606/213, 216–218
See application file for complete search history.

(56) References Cited

U.S. PATENT DOCUMENTS 3,874,388 A *  4/1975  King et al. ..................... 606/232
5,334,217 A     8/1994  Das
(Continued)

FOREIGN PATENT DOCUMENTS

JP    2000-505668 A    5/2000
JP    2002-119515 A    4/2002
(Continued)

OTHER PUBLICATIONS

International Search Report for PCT/JP2006/306294 dated Jun. 27, 2006.
(Continued)

*Primary Examiner* — Julian W Woo
(74) *Attorney, Agent, or Firm* — Buchanan Ingersoll & Rooney P.C.

(57) ABSTRACT

Provided is a defect-closure device which is surely retainable in a predetermined position to close a passage-like defect in a living body. The device may have a free enlargement-contraction first member mounted so as to close an opening at the one end of the defect; and a free enlargement-contraction second member having a protruded member, which extends from a joint part jointed to the first member, and protrudes from an opening at the other end in an axis direction of the defect. The first member is elastically contacted to the opening by elastically contacting a protrusion part of a second member to the inner surface of an edge of the opening.

15 Claims, 11 Drawing Sheets

(56) References Cited

U.S. PATENT DOCUMENTS

| | | |
|---|---|---|
| 5,433,727 A | 7/1995 | Sideris |
| 5,578,045 A | 11/1996 | Das |
| 5,709,707 A | 1/1998 | Lock et al. |
| 6,036,720 A * | 3/2000 | Abrams et al. ............... 606/213 |
| 6,063,070 A * | 5/2000 | Eder ............................... 606/1 |
| 6,077,281 A | 6/2000 | Das |
| 6,174,322 B1 | 1/2001 | Schneidt |
| 6,214,029 B1 | 4/2001 | Thill et al. |
| 6,355,052 B1 | 3/2002 | Neuss et al. |
| 6,440,152 B1 | 8/2002 | Gainor et al. |
| 6,551,344 B2 | 4/2003 | Thill |
| 7,011,094 B2 * | 3/2006 | Rapacki et al. ......... 128/207.15 |
| 7,431,729 B2 * | 10/2008 | Chanduszko ................. 606/213 |
| 7,569,066 B2 * | 8/2009 | Gerberding et al. .......... 606/200 |
| 7,582,104 B2 * | 9/2009 | Corcoran et al. ............. 606/215 |
| 2002/0183787 A1 | 12/2002 | Wahr et al. |
| 2003/0195530 A1 | 10/2003 | Thill |
| 2003/0220667 A1 | 11/2003 | Van Der Burg et al. |
| 2003/0225421 A1 | 12/2003 | Peavey et al. |
| 2005/0065546 A1 | 3/2005 | Corcoran et al. |
| 2005/0065547 A1 | 3/2005 | Marino et al. |

FOREIGN PATENT DOCUMENTS

| | | |
|---|---|---|
| JP | 2002-119516 A | 4/2002 |
| JP | 2002-248105 A | 9/2002 |
| JP | 2002-355248 A | 12/2002 |
| JP | 2004-528131 A | 9/2004 |

OTHER PUBLICATIONS

English language translation of International Preliminary Report on Patentability issued in PCT/JP2006/306294, 2006.

European Communication and Supplementary Search Report dated Mar. 11, 2014 issued in the corresponding European Patent Application No. 06730242.2-1654/1864613 (11 pages).

International Preliminary Report on Patentability and English language translation of same, 2007.

* cited by examiner

DEFECT-CLOSURE DEVICE AND DELIVERY APPARATUS

TECHNICAL FIELD

The present invention relates to a defect-closure device for closing a defect generated in a living body, and a delivery apparatus.

BACKGROUND ART

Recently, Patent Foramen Ovale (hereafter referred to as PFO) is noted as cardiogenic cause of stroke or migraine. PFO is a symptom of still opening a patent foramen ovale, which provides left-to-right blood shunt in a heart in infancy, even after grownup to an adult, and from 20 to 30% of adults are said to have.

A patent foramen ovale generates at a septum secundum of a heart, and is occluded by a septum primum in a usual heart, due to higher left atrial pressure than right atrial pressure, however, in tension (for example in coughing or holding on), higher right atrial pressure than left atrial pressure results in opening of a septum primum toward a left atrial side, and blood flowing from a right atrial side (a vein side) to a left atrial side (an arterial side). In the case where blood clots are contained in this blood, the blood clots result in to move from a vein side to an arterial side, and flow in a direction of a left atrial→a left ventricle→an aorta→a brain, thus causing stroke or migraine.

As treatments for such diseases, a drug therapy (aspirin, warfarin), a closing operation of a patent foramen ovale by percutaneous catheter technique, and an open-heart operation by extracorporeal circulation are included. The drug therapy is a first choice treatment, however, has a problem that control of administration amount is difficult and cessation of bleeding is difficult during administration. The percutaneous catheter technique and the open-heart operation accompany invasion, however, possibility of relapse is none due to being a radical operation. At a present stage, as for an occlusion technique, the open-heart operation is considered to be surer, however, in consideration of also risk in carrying out extracorporeal circulation, and large area of invasion in skin incision, treatment by percutaneous catheter technique is a desirable method as long as similar effect as by the open-heart operation can be obtained.

A device for the closing technique using a percutaneous catheter can also be used in closing a passage-like defect such as a congenital type of atrial septal defect (ASD), PFO, ventricular septal defect (VSD), and patent ductus arteriosus (PDA), and the following ones are included as such a device.

For example, to close a defect, one for sandwiching a disk-like membrane by indwelling at each of a left atrial side and a right atrial side (see abstract, paragraphs 0022 and 0023, and FIG. 1 of JP-A-2002-355248; see paragraph 0010, and FIG. 2 of JP-A-2002-248105; see abstract, paragraphs 0035 and 0036, and FIG. 1 of JP-A-2002-119516; see abstract and FIG. 1 of US-2003-195530A; and see abstract of U.S. Pat. No. 6,174,322); one for sandwiching by using an anchoring member formed by a wire rod at one end, and a disk-like membrane at the other end (see paragraphs 0037 and 0042, and FIGS. 11, 11A and 11C of JP-2004-528131A); or one for sandwiching by using an anchoring member formed by wire rods at both ends (see abstract and FIG. 4 of US-2003-225421A); or the like.

However, use of a pair of disk-like membranes make a structure complicated and increases area of a foreign material, which tends to easy adherence of blood clots; in particular, adherence of blood clots onto a disk-like membrane at the left atrial side could cause stroke by flowing thereof, and could break a septum primum having thin thickness.

Use of a disk-like membrane member or an anchor member made of a wire material also raises a problem, in the case of a indwelling and sandwiching system onto each of the left atrial side and the right atrial side, of generation risk of displacement due to non-fixed position thereof, and being not a structure for surely retaining thereof at the predetermined position.

In addition, the above-described device is delivered and indwelled from a vein of a femoral region to inside the cardiovascular, and a delivery apparatus is used to carry out delivery and release of such a device. A delivery apparatus usually uses a catheter for storing a device inside the catheter, and releasing a device after delivery to the predetermined position.

Conventional delivery apparatuses carry out a device release by using a screw mechanism, which exerts force on a device itself at device releasing, resulting in displacement of indwelling position, or deformation of tissue of a part for mounting, or could deviate the device to the left atrial side, and thus a sure and safe indwelling state could not be obtained in some cases.

SUMMARY OF THE INVENTION

The present invention is made to solve the above-described problems, and thus it is an object of the present invention to provide a defect-closure device which has small area, and fixed position even in indwelling, and is surely retained in the predetermined position and has a simple configuration, and a delivery apparatus.

A defect-closure device of the present invention for attaining the above object, in a defect-closure device for closing a passage-like defect in a living body, has a free enlargement-contraction first member mounted so as to close an opening at the one end of the defect, and a free enlargement-contraction second member having a protruded part which extends from a joint part jointed to the first member and protrudes from an opening at the other end in an axis direction of the defect, characterized in that the first member is elastically contacted to the opening by elastically contacting the protrusion part of the second member to the inner surface of the opening edge of the opening.

In addition, the present invention, in a defect-closure device for closing the device in a state that an opening of a passage-like defect in a living body is covered with a septum, has a free enlargement-contraction first member pushing the septum to the opening, and a free enlargement-contraction second member mounted at the opening side by being jointed to the first member, via a joint part, characterized in that the first member pushes the septum so as to close the opening by elastically contacting the second member to the inner surface of the opening edge of the opening.

Furthermore, the present invention, in a delivery apparatus for storing a defect-closure device for closing a passage-like defect in a living body, having a free enlargement-contraction first member, and a free enlargement-contraction second member jointed to the first member, via a joint part, inside a catheter, and delivering thereof, has a pusher part, which has an inner cylinder mounted inside said catheter, and a hooking member mounted at the tip part of said inner cylinder; and an operation wire inserted through the inner cylinder so as to enable forward-backward movement; characterized in that the operation wire, which is protruded from the inner cylinder, forms an engaging state by inserting through a part of the closing device during inserting through inside a loop of the hooking member, and makes the closing device in a released state, by making the operation wire retreated from inside the loop of the hooking member.

In the present invention, because the base end part is jointed to the first member, and the protrusion part of the second member, which is protruded from this base end part, is elastically contacted to the inner surface of the opening edge of a passage-like defect at the middle part thereof so that the first member closes the opening, the first member takes aligning itself relative to the opening due to the elastic contact of the second member, and takes a concentric arrangement state with the opening. Therefore, sure closure of the opening can be secured even for the second member having size equivalent to the opening, and only minimal area is required and generation of blood clots can be prevented. In the case where this device is indwelled, because the protrusion part is positioned inside the opening of the passage-like defect, it can be securely maintained at a fixed and predetermined position. At the same time, because only one side can be closed without closing the opening at the both ends in an axis direction of the passage-like defect by sandwiching from the both sides, configuration can be extremely simple.

In addition, a delivery apparatus is capable of, in delivering, storing a whole device in a catheter and safely delivering, and, in indwelling, capable of releasing the closing device only by retreating an operation wire from inside the loop of a hooking member, and thus a sure and safe indwelling state can be obtained without adding any force onto the closing device or a peripheral tissue, and without generating displacement of an indwelling position, deformation of the tissue, unfastening of the device or the like.

Further other objectives, features and characteristics of the present invention will be made clear with reference to the following explanation and preferable embodiments exemplified in the accompanying drawings.

BEST EMBODIMENTS FOR CARRYING OUT THE INVENTION

Explanation will be given in detail on embodiments of the present invention with reference to drawings.

A First Embodiment

Figure 1:
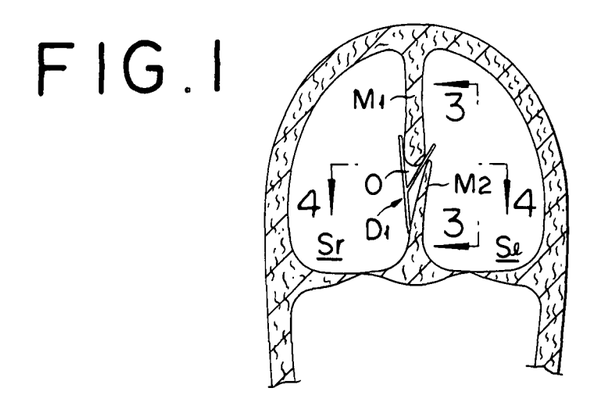
FIG. 1 is a schematic cross-sectional view showing a mounted state of a defect-closure device relevant to a first embodiment of the present invention, onto a defect part.
Figure 2:
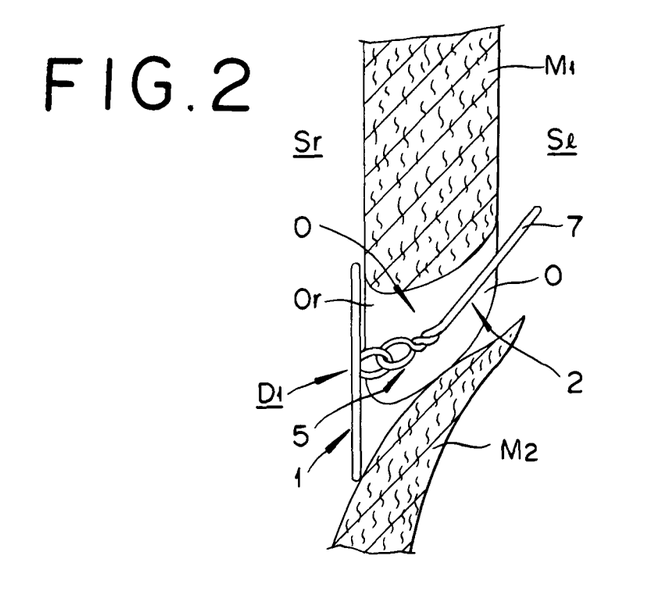
FIG. 2 is an enlarged view of substantial parts of FIG. 1.
Figure 3:
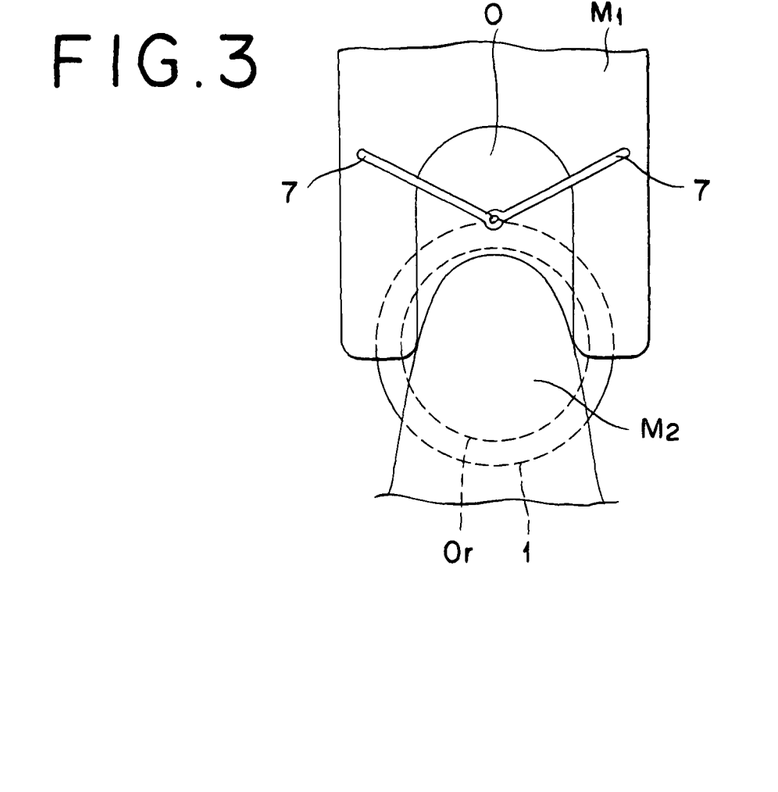
FIG. 3 is an arrow view along the 3-3 line of FIG. 1.
Figure 4:
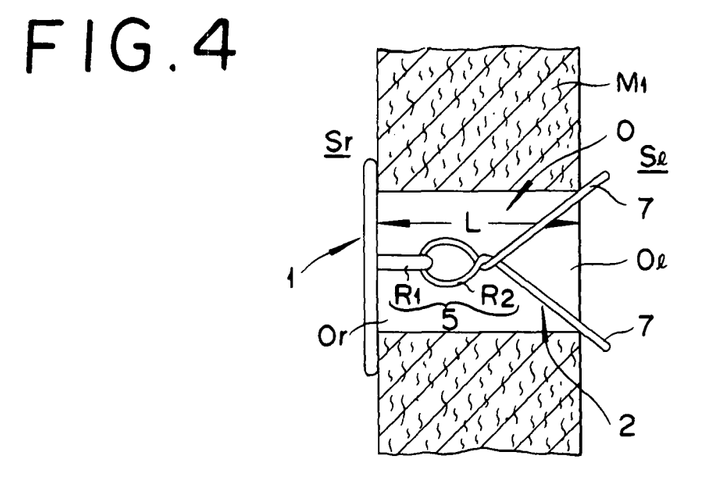
FIG. 4 is a cross-sectional view along the 4-4 line of FIG. 1.
Figure 5:
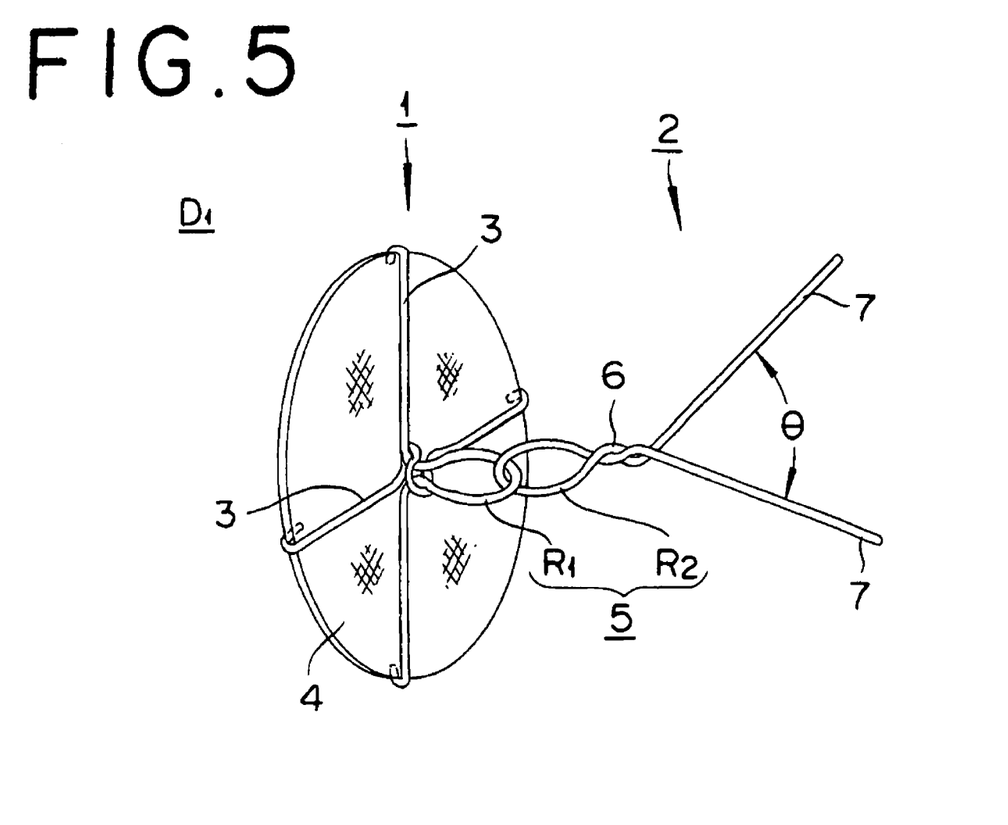
FIG. 5 is a perspective view showing a defect-closure device relevant to the above embodiment.

FIG. 1 is a schematic cross-sectional view showing a mounted state of a defect-closure device relevant to a first embodiment of the present invention, onto a defect part. FIG. 2 is an enlarged view of substantial parts of FIG. 1. FIG. 3 is an arrow view along the 3-3 line of FIG. 1. FIG. 4 is a cross-sectional view along the 4-4 line of FIG. 1. FIG. 5 is a schematic perspective view showing the present embodiment. It should be noted that FIGS. 2 to 4 show a defect part or a wire rod in a kind of an exaggerated way to provide easier viewing.

The defect-closure device of the present embodiment is used, for example, in treatment of closing a defect of PFO, however, as shown in FIG. 1, in the case where the passage-like defect O, which is a patent foramen ovale, is generated at the septum secundum M1 of a heart, only an opening at one end of the defect O is closed.

It should be noted that, in the present specification, "the passage-like defect O" includes not only one being relatively long in an axis direction, like a so-called passage, but also one like a hole being extremely short in this length.

As an opening to be closed, as shown in FIG. 2, the opening Or at the right atrial Sr side is preferable. It is because, in a usual heart, the defect O is occluded by a septum primum M2 due to higher left atrial pressure than right atrial pressure; and in tension (for example in coughing or holding on), higher right atrial pressure than left atrial pressure results in opening of a septum primum toward a left atrial side, and blood flowing from a right atrial side (a vein side) to a left atrial side (an arterial side), and thus generation of blood clots transfer can be prevented. It should be noted that "Ol" in the drawing represents an opening at the left atrium Sl side.

The defect-closure device D1 of the present embodiment, in general, closes the opening Or at the right atrium Sr side of the passage-like defect O, by the first member 1, which is a sheet of a membrane-like member, and generates closing force of the first member 1, by the second member 2, which is a kind of spring-like member jointed to the first member 1. The second member 2 elastically contacts to the inner surface of the opening edge of the opening Ol at the left atrium Sl side, and fulfills automatic aligning function so that the first member 1 is concentrically arranged with the defect O.

Further more detailed explanation will be given. The defect-closure device D1 of the present embodiment has, as shown in FIG. 2, the first member 1 for closing the opening Or at the right atrial Sr side of the defect O, and the second member 2 whose base end part is jointed to the first member 1 via the joint part 5.

The first member 1 is, as shown in FIG. 5, a membrane-like member, wherein two extremely slender and elastic skeleton wire rods 3 are jointed in a cross-shape, and the membrane body 4 is mounted onto the skeleton wire rods 3. The device D1, which will be described in detail, because it is stored in the slender catheter 10 in a contracted state, and delivered to a defect position, then taken out from the catheter 10 at the defect position to enlarge and close the opening Or, forms a skeleton by the extremely slender and elastic skeleton wire rods 3, and designed to be free enlargement-contraction.

However, the skeleton wire rods 3 may be not only simple two pieces, but also further many pieces, and one piece may be formed into a ring shape, and this may be jointed with a radially extending wire rod depending on a case. It is preferable, in any way, that the skeleton wire rods 3 are positioned in the same plane in an enlarged state. In this way, they are capable of deforming from thus enlarged plane state, in response to concavity and convexity of the opening edge part of the opening Or having various shapes, by which a closed state of the opening Or becomes surer.

As a specific example of the skeleton wire rods 3, it is preferable to use a metal wire of such as stainless steel, nickel-titanium, an ultra elastic alloy (such as a Ni—Ti alloy) or the like, with a diameter of about from 0.1 mm to 0.5 mm. As the membrane body 4, it is preferable to use a thin membrane of such as polyester woven fabric, PTFE, ePTFE, urethane or the like. To the membrane body 4, a French seam for inserting through the skeleton wire rods 3 may be provided for jointing the membrane body 4 and the skeleton wire rods 3, or a folding part or a loop part may be formed at outer end of the skeleton wire rods 3, to secure jointing with the membrane body 4. It is preferable, in anyway, that a sharply pointed extremity does not protrude outward.

The second member 2 is, as shown in FIG. 5, formed by using one wire rod similar to the above-described skeleton wire rods 3, as a whole, and by clinching thereof. At the base end part, the joint part 5 is formed, which is jointed to the first member 1; at the middle part, the twisted member 6 is provided; and at the other end part, the protrusion part 7 is provided. In the second member 2 of the present embodiment, the base end part is formed in a loop state, and the protrusion part 7 is protruded in an angle state, wherein a pair of wire rods have a predetermined angle of θ, so that spring function is fulfilled as a whole.

Therefore, the defect-closure device D1 of the present embodiment is, as shown in FIGS. 3 and 4, capable of following length variation in an axis direction of the passage-like defect O, caused by size of the defect O or individual difference, because the second member 2 elastically contacts with the inner surface of the opening edge of the opening Ol at the left atrium Sl side, and also capable of fulfilling automatic aligning function; and the first member 1 is designed, as shown by the broken line of FIG. 3, so that the opening Or of the defect O and the first member 1 are concentrically arranged.

The joint part 5 may be any type as long as being capable of jointing the first member 1 and the second member 2, for example, may be configured by the loop-like part R1 formed at the center part of one of the skeleton wire rod 3 of the first member 1, and the loop-like part R2 formed at the base end part of the second member 2, so that one of the both loop-like parts R1 and R2 inserts through the other.

In this way, the joint part 5 is capable of making one of the first member 1 and the second member 2 rotated or inclined relative to the other, and in the same manner as one wherein the first member 1 and the second member 2 are jointed by a universal joint, capable of accurately closing the opening Or without influence of one of the inclined displacement state on the other, and also capable of following length variation in an axis direction of the passage-like defect O caused by individual difference, substantially thickness variation of the septum secundum M1.

In addition, the joint part 5 is useful in determination of distance L between the first member 1 and a part where the second member 2 contacts with the inner surface of the opening edge of the opening Ol, in consideration of thickness of the septum secundum M1. The joint part 5 may have no length in an axis direction of the defect O, namely, may be "0", however, formation of the loop-like part as above makes setting easy to the above distance L in response to thickness of the septum secundum M1, which results in influencing on closing force of the first member 1 by spring force of the second member 2.

The protrusion part 7 at the other end is a part, which elastically contacts with the inner surface of the opening edge of the opening Ol at the left atrium Sl side, and thus it is preferably apart so that a mutual center angle has the predetermined angle. The mutual center angle between both of the protrusion parts 7 is one to be determined depending on size of the defect O, thickness of the septum secundum M1 or the like. It should be noted that the present embodiment has two protrusion parts 7, however, it is not limited thereto, as long as being a plurality of pieces.

Figure 6:
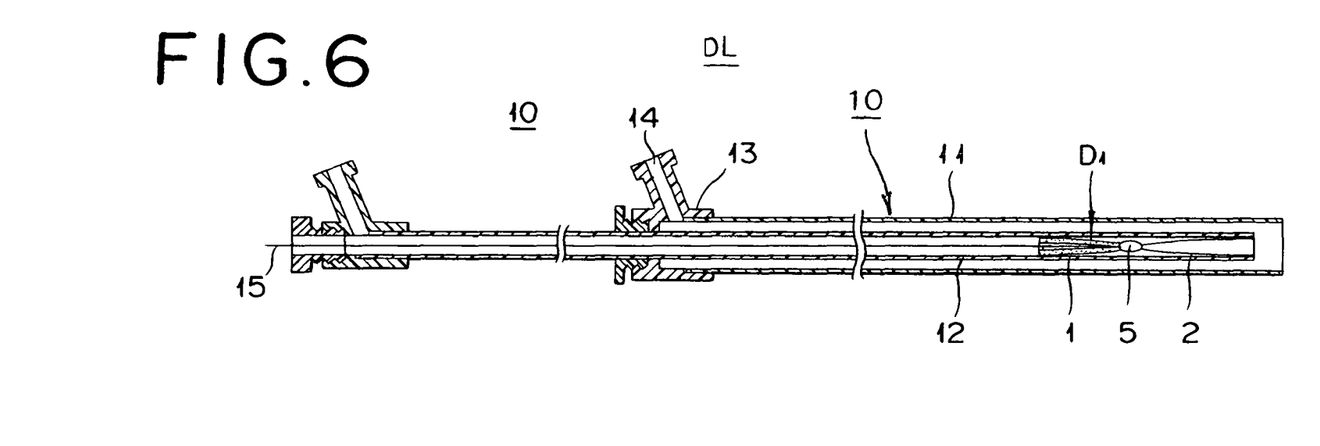
FIG. 6 is a cross-sectional view showing an example of a catheter storing the present device.
Figure 7:
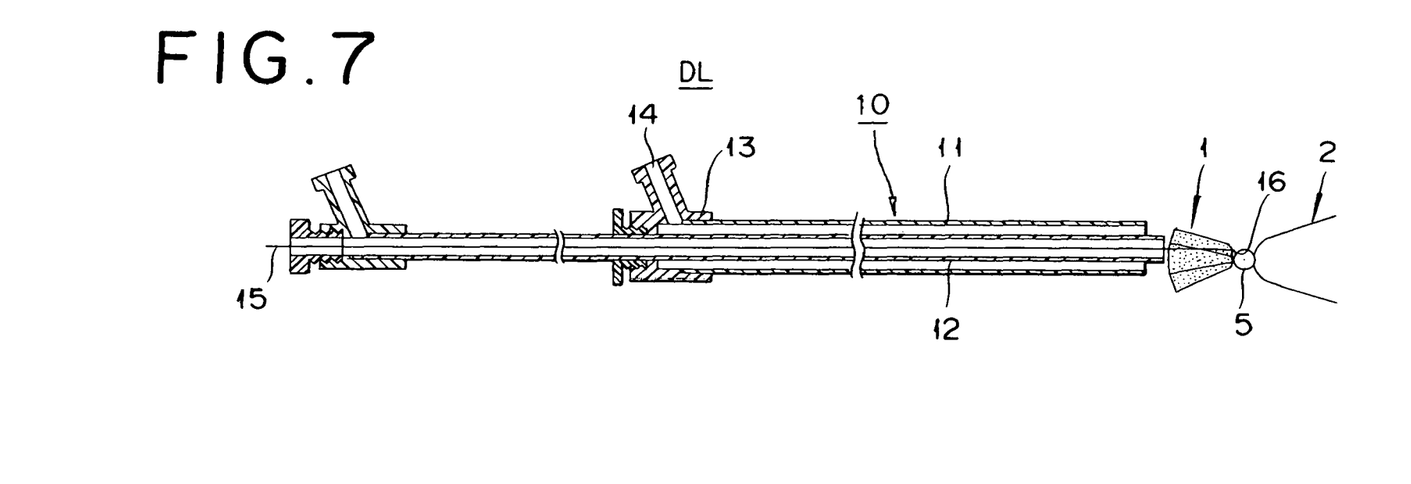
FIG. 7 is a cross-sectional view showing a protruded state of the present device from the above catheter.

FIG. 6 is a cross-sectional view showing an example of a delivery apparatus for storing and delivering the present device. FIG. 7 is a cross-sectional view showing a protruded state of the device from the delivery apparatus.

The delivery apparatus DL has the catheter 10, and the catheter 10 is configured by the outer cylinder 11 and the inner cylinder 12 made of a relatively flexible synthetic resin; at the base end part of the outer cylinder 11, the Y connector 13 is provided; and the side port 14 of the Y connector 13 is communicated with a space part between both cylinders. It should be noted that the side port 14 is used for insertion of a guide wire (not shown) for guiding the catheter 10 up to the passage-like defect O, or for infusion of a drug solution, or the like.

The inner cylinder 12 is inserted through the Y connector 13 and extended, and at the inside thereof, the operation wire 15 for operating the device D1 is provided. The operation wire 15 is provided with the engaging-releasing unit 16 (see FIG. 7) at the tip part, jointed with the joint part 5 of the device D1, and by forward-backward movement inside the inner cylinder 12, the device D1 is designed to appear from the tip of the inner cylinder 12. Therefore, the operation wire 15 may be any type as long as enabling forward-backward movement of the device D1 inside the inner cylinder 12, however, it is preferable to use, for example, a stainless wire, an Ni—Ti wire or the like.

The engaging-releasing unit 16 is one for releasing the device D1 inside the inner cylinder 12, at the predetermined position, after extruding from the tip of the inner cylinder 12, and is configured by, for example, one where a hook part is formed by folding the tip of the operation wire 15 in a U-character shape. The hook part is capable of delivering the device D1 in an engaged state to the joint part 5, and unlocking the engagement to the joint part 5 by rotating the operation wire 15 around the axis, in releasing.

Explanation will be given next on action of the present embodiment.

Figure 8:
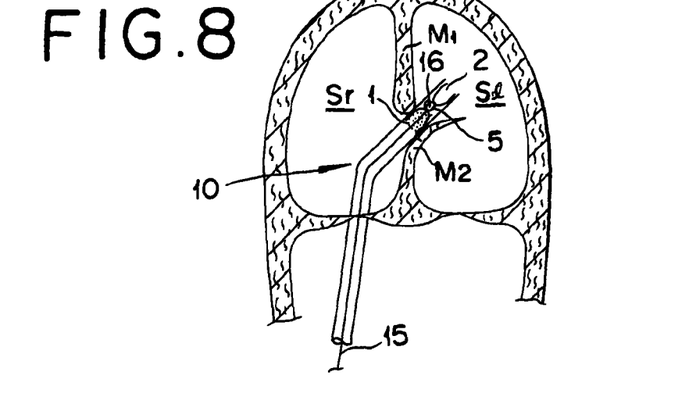
FIG. 8 is a cross-sectional view showing a mounted state of a catheter onto a defect part.
Figure 9:
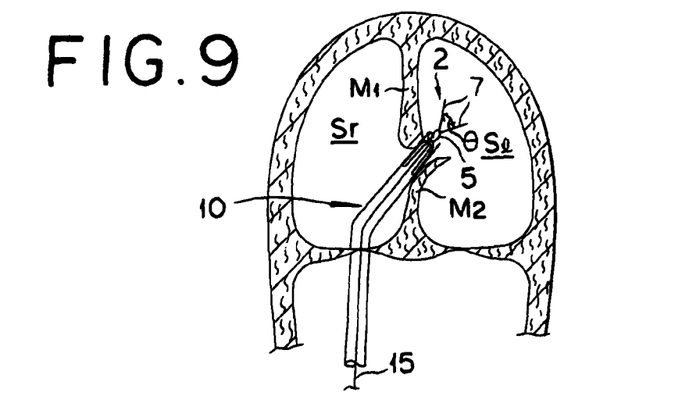
FIG. 9 is a cross-sectional view showing a protruded state of a first member from a catheter.
Figure 10:
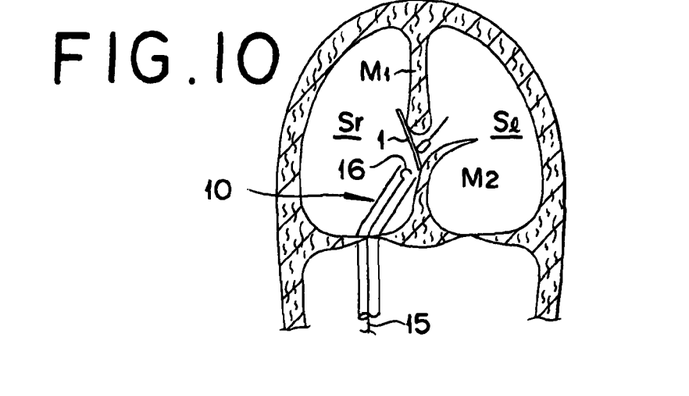
FIG. 10 is a cross-sectional view showing a protruded state of a device from a catheter.

FIG. 8 is a cross-sectional view showing a mounted state of a catheter onto a defect part. FIG. 9 is a cross-sectional view showing a protruded state of the first member from the catheter. FIG. 10 is a cross-sectional view showing a protruded state of a device from the catheter.

First of all, an operator inserts the operation wire 15 inside the inner cylinder 12 of the catheter 10, and protrudes the engaging-releasing unit 16 from the tip to engage with the joint part 5 of the device D1. Then, the first member 1 and the second member 2 of the device D1 are contracted to be stored inside the inner cylinder 12, the first member 1 being firstly, and subsequently the second member 2 is drawn in.

In this state, a guide wire is inserted from the side port 14 of the Y connector 13 to insert and fix the tip of the guide wire up to the left atrium Sl in a heart. After inserting the tip of the catheter 10 up to the left atrium Sl with a help of this guide wire as a guide, only the guide wire is drawn out (see FIG. 8).

Then the operation wire 15 is operated to extrude the second member 2 of the device D1 from the inner cylinder 12. By this extrusion, the second member 2 is released from restriction by the inner cylinder 12, and becomes an enlarged state by own elasticity (see FIG. 9).

When the catheter 10 is retreated a little from the inside of the left atrium Sl, and the tip thereof enters the right atrium Sr side, the second member 2 in an enlarged state elastically contacts with the inner surface of the opening edge of the opening Ol at the left atrium Sl side of the passage-like defect O. In particular, because the protrusion part 7 of the second member 2 is enlarged into a folding-fan shape having a predetermined center angle of θ, elastic repulsion force of each of the protrusion parts 3 uniformly acts at the inner surface of the opening edge of the opening Ol. In addition, because the joint part 5 joints the second member 2 to the first member 1 in a free inclination-deformation manner, the second member 2 itself results in displacing to take nearly a center position.

At this stage, the operation wire 15 is rotated to unlock engagement between the engaging-releasing unit 16 and the joint part 5, and then by further retreating the catheter 10, the first member 1 is drawn out from the catheter 10, because the second member 2 is contacted with the inner surface of the opening edge of the opening Ol, however, the second member 2 receives tension force at this time, resulting in taking a more center position (see FIG. 10).

The first member 1 thus drawn out enlarges by own elasticity, and is pulled by elastic force of the second member 2 to occlude the opening Or. Even in the case where the opening Ol of the left atrial side and the opening Or of the right atrial side of the defect O are displaced, it can be eliminated by rotation or inclined deformation of the joint part 5 between the first member 1 and the second member 2. As a result, the middle part of the protrusion part 7 of the second member 2 elastically connects to the inner surface of the opening edge of the opening Ol to fulfill automatic aligning function, and the first member 1 is concentrically arranged with the defect O, and thus the first member 1 closes the opening Or of the right atrial side of the defect O.

In this way, in the present embodiment, because only the right atrial side of the defect O is closed by a membrane-like member, the defect O can be closed by extremely simple configuration, and a small contact part with blood results in prevention of blood clot generation. Moreover, because the protruded part is positioned inside the opening of a passage-like defect, the device D1 is surly retained at the fixed and the predetermined position, even when being indwelled.

A Modified Example

Figure 11:
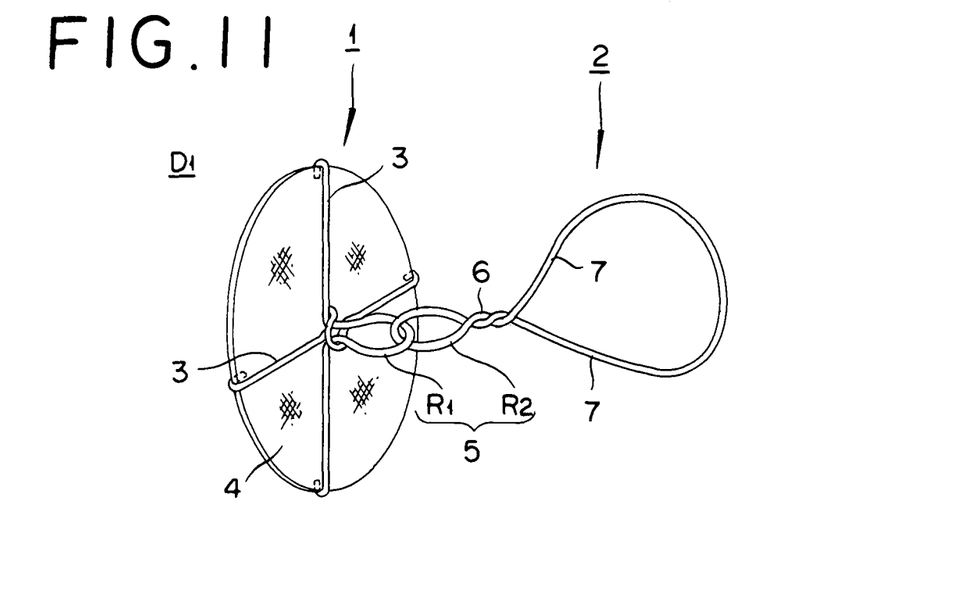
FIG. 11 is a perspective view showing a modified example of the first embodiment.

FIG. 11 is a schematic perspective view showing a modified example of the present embodiment. It should be noted that the same codes are attached to members common to the members shown in FIG. 1 and the like to omit explanation. In the above embodiment, the protrusion part 7 of the second member 2 is radially protruded, however, as shown in FIG. 11, the second member 2 may be a wire rod formed in a circular shape or a loop shape. In this way, extreme safety is attained, because of no generation of a sharp end part, even when a slender wire rod is used at a constantly moving part like a heart.

A Second Embodiment

Figure 12:
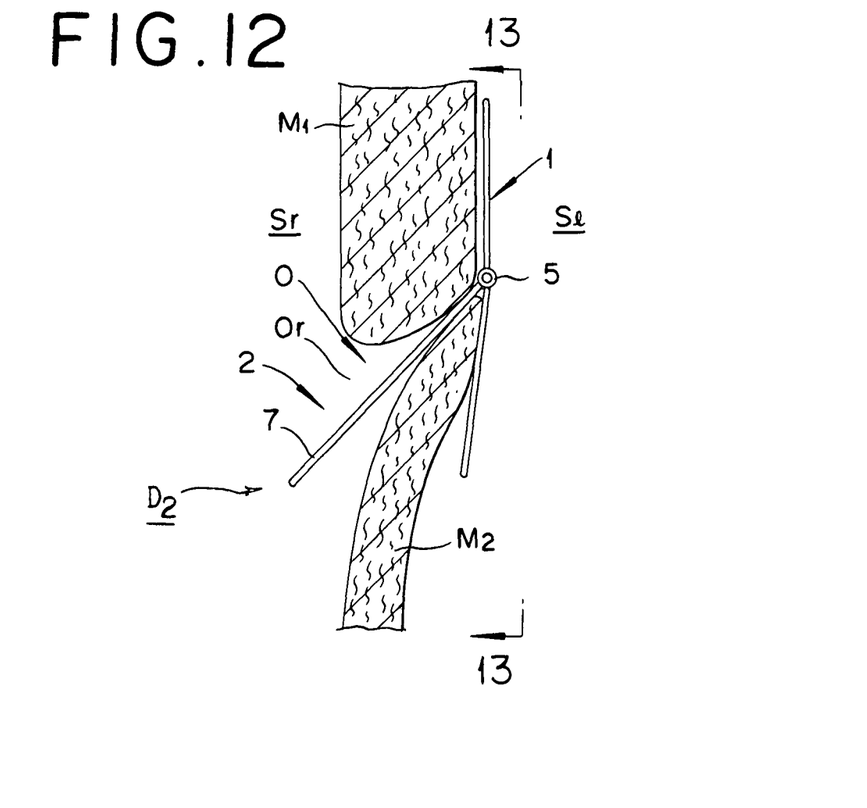
FIG. 12 is a cross-sectional view of important parts showing a mounted state of a defect-closure device relevant to a second embodiment of the present invention, onto a defect part.
Figure 13:
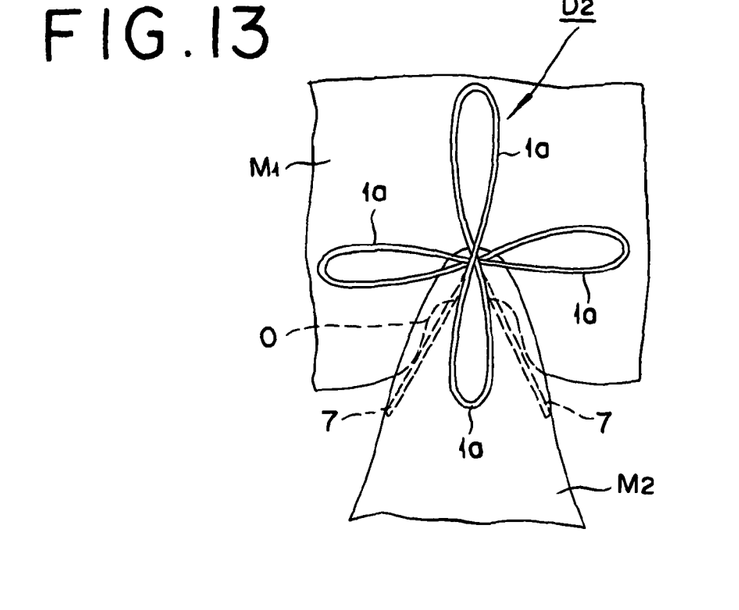
FIG. 13 is an arrow view along the 13-13 line of FIG. 12.
Figure 14:
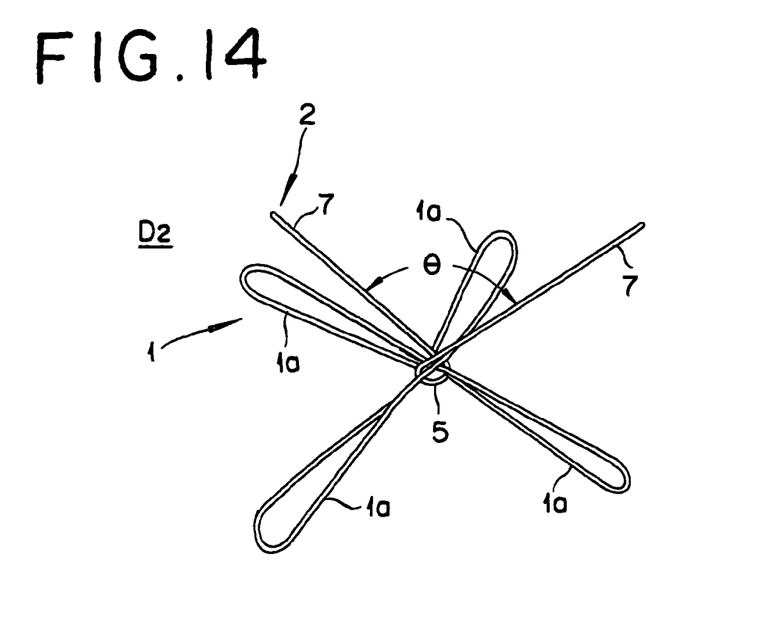
FIG. 14 is a schematic perspective view showing the second embodiment of the present invention.

FIG. 12 is a cross-sectional view of important parts showing a mounted state of a defect-closure device relevant to the second embodiment of the present invention, onto a defect part. FIG. 13 is an arrow view along the 13-13 line of FIG. 12. FIG. 14 is a perspective view of the defect-closure device relevant to the second embodiment. It should be noted that the same codes are attached to members common to the members shown in FIGS. 1 to 11 to omit explanation.

As shown in FIG. 12, in the case where the defect O generated at the septum secundum M1 of a heart is constantly closed by the septum primum M2, the defect-closure device D2 of the present embodiment is suitable as a support tool for supporting closure of the septum primum M2.

The defect-closure device D2 also has the first member 1 and the second member 2, however, as shown in FIG. 14, any of the both members is configured by extremely slender elastic wire rods 3.

The first member 1 has a plurality of radial protrusion parts 1a formed in a flat and slender propeller-blade shape. However, it is not limited thereto, and may be one having one piece of the radial protrusion part 1a, or further more numbers may be concentrically arranged; in addition, it may be one where an opposite pair of radial protrusion parts 1a may be formed in an "8" character shape.

On the other hand, the second member 2 has the joint part 5 for bundling a plurality of radial protrusion parts 1a at the center part, and from the joint part 5, in the same manner as one described above, the protrusion parts 7 are protruded in a pair of an angle state with a predetermined center angle of θ. The joint part 5 does not have relatively long predetermined length as the above-described embodiment, however, it may naturally be one having the predetermined length in some cases.

It should be noted that as for the second member 2 of the present embodiment also, it may be one having one piece of a ring-like shape in some cases, in the same manner as in the above-described modified example.

In the defect-closure device D2 of the present embodiment, as shown in FIG. 12 and FIG. 13, the middle part between the base end and the tip of the protrusion part 7 in the second member 2 is elastically contacted to the inner surface of the opening edge of the opening Or at the right atrium Sr side of the defect O, so as to push the septum primum M2 by the first member 1 from the left atrium Sl side of the defect O. Due to this elastic contact to inner surface of the opening edge of the protrusion part 7, automatic aligning function is fulfilled also in the present embodiment; and the first member 1 is designed to be concentrically arranged with the defect O, and this aligning function is not for making a good closing state of the defect O, as in the first embodiment, but rather for preventing displacement of the first member 1.

In this way, the defect-closure device D2 of the present embodiment is designed to surely close the defect O of a heart, because the second member 2 supports closure of the septum primum M2 at the left atrium Sl side.

It should be noted that the defect-closure device D2 of the present embodiment is designed to insert the second member 2 first, in storing in a catheter so that the first member 1 is positioned at the tip. Taking out in usage may be carried out in the same manner as in the previous embodiment.

A Third Embodiment

Figure 15:
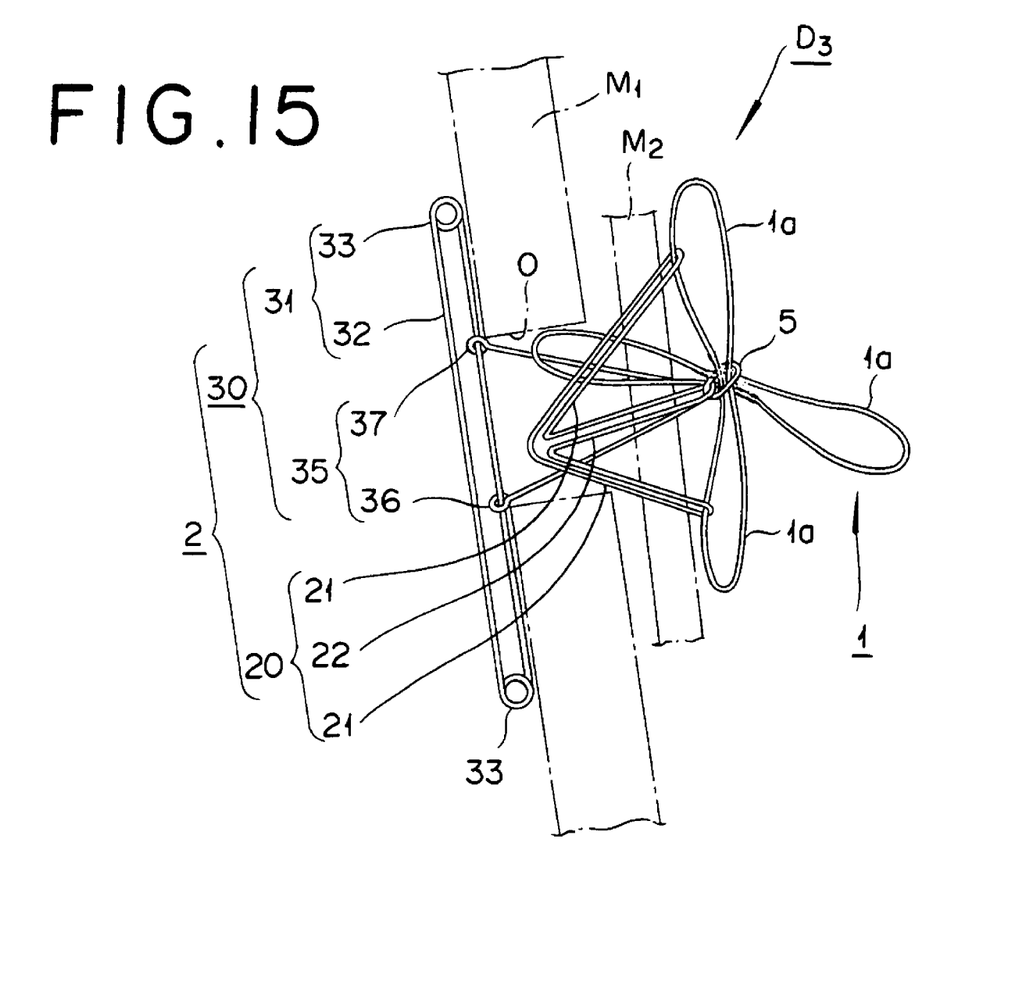
FIG. 15 is a perspective view showing a third embodiment of the present invention.
Figure 16:
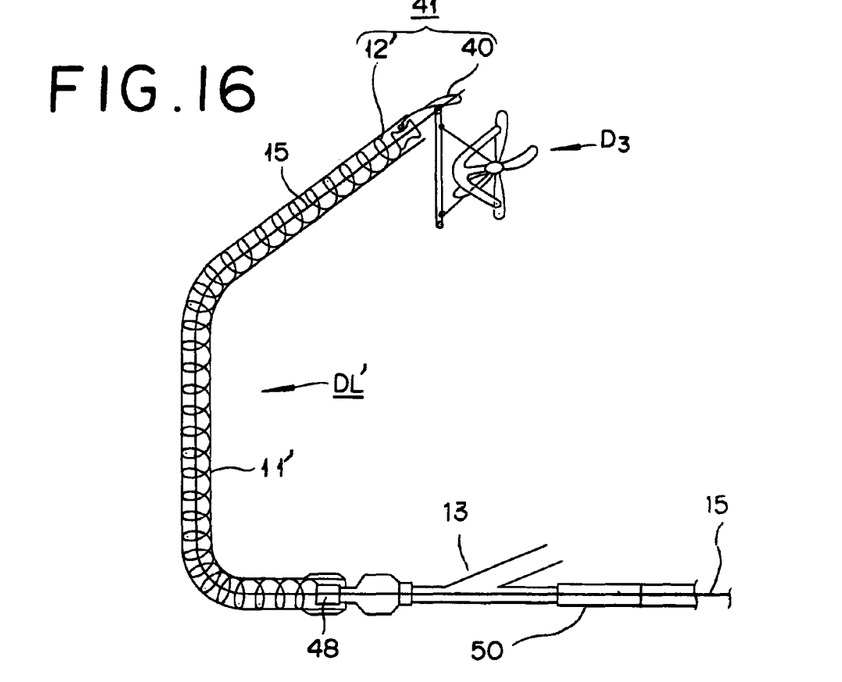
FIG. 16 is a cross-sectional view showing a mounted state of the above device onto a delivery apparatus.
Figure 17:
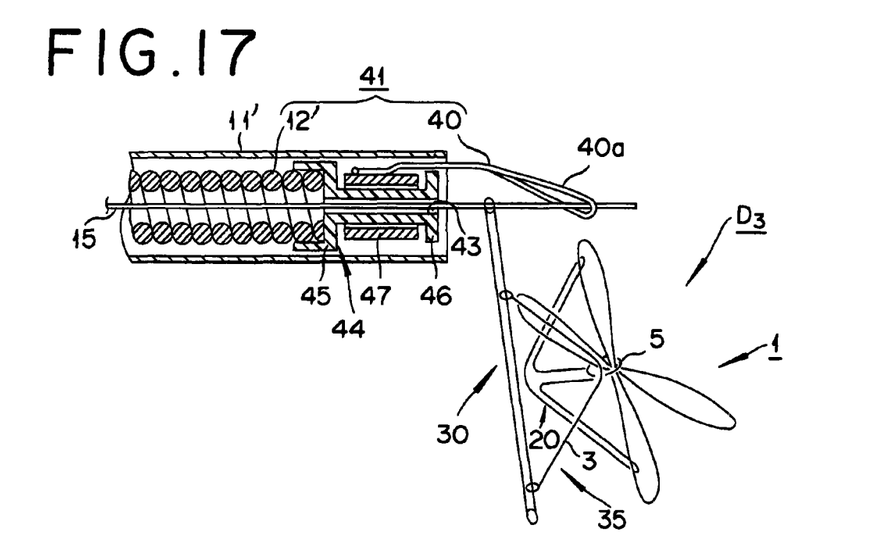
FIG. 17 is an enlarged view of substantial parts of FIG. 16.
Figure 18:
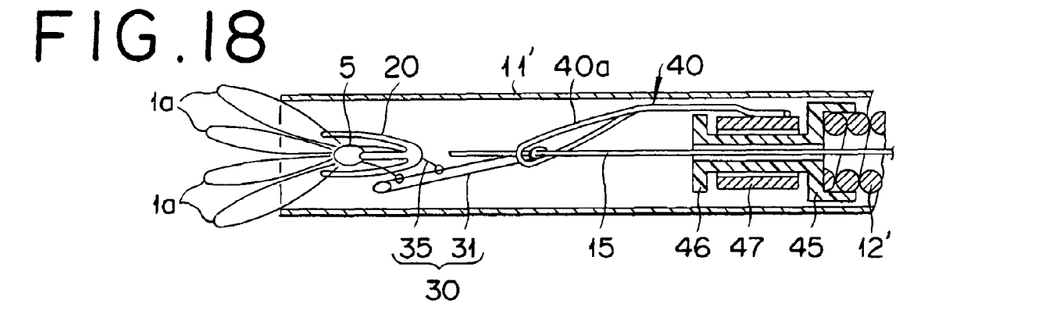
FIG. 18 is a cross-sectional view showing a state just before storing the above device into a delivery apparatus.
Figure 19:
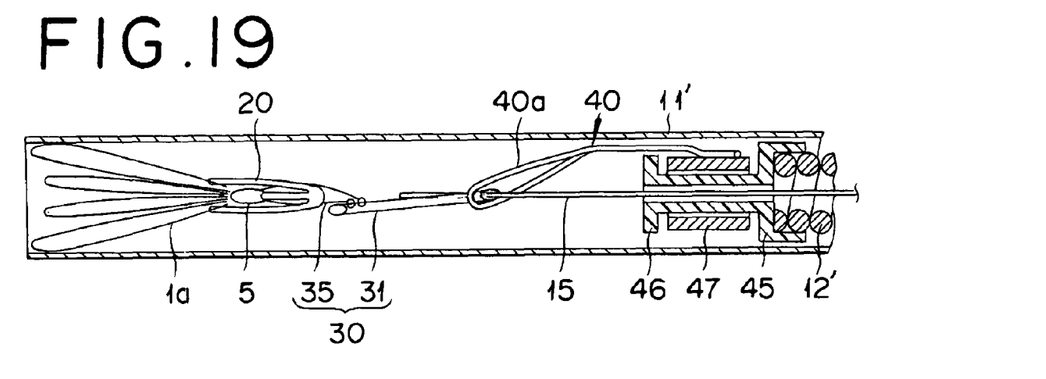
FIG. 19 is a cross-sectional view showing a storing state the above device into a delivery apparatus.
Figure 20:
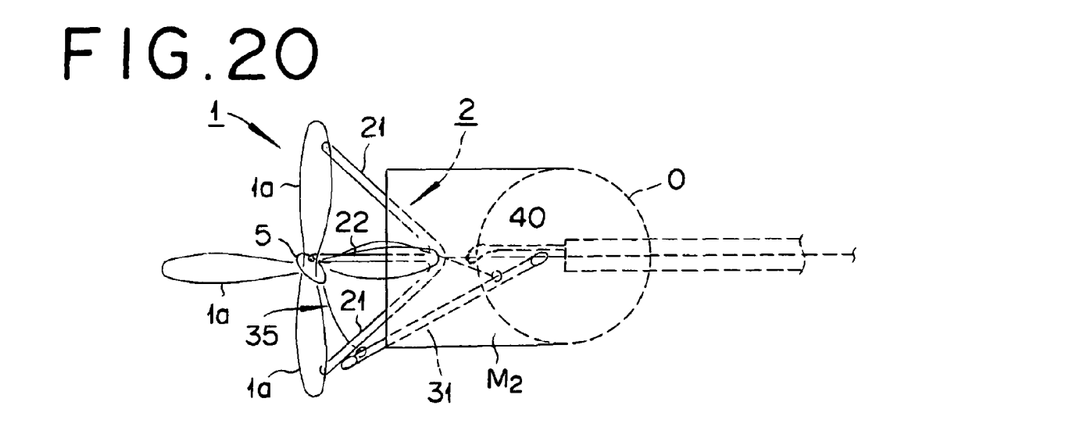
FIG. 20 is a view showing a mounted state of a device onto a defect part, seen from a right atrial side.
Figure 21:
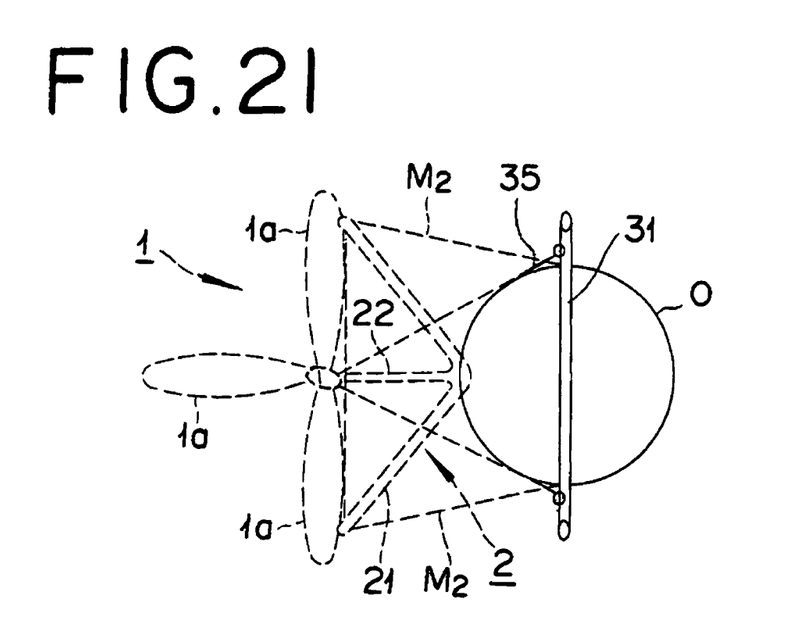
FIG. 21 is a view showing a mounted state of the above defect-closure device, seen from a left atrial side.

FIG. 15 is a perspective view showing a defect-closure device relevant to the third embodiment of the present invention. FIG. 16 is a cross-sectional view showing a mounted state of the above defect-closure device onto a delivery apparatus. FIG. 17 is an enlarged cross-sectional view of substantial parts of FIG. 16. FIG. 18 is a cross-sectional view showing a state just before storing the above defect-closure device into the delivery apparatus. FIG. 19 is a cross-sectional view showing a storing state the above defect-closure device into the delivery apparatus. FIG. 20 is a view showing a mounted state of the defect-closure device, seen from a right atrial side. FIG. 21 is a view showing a mounted state of the above defect-closure device, seen from a left atrial side. It should be noted that the same codes are attached to members common to the members shown in FIG. 1 and the like to omit explanation.

The defect-closure device D3 of the present embodiment is, in the same manner as in the second embodiment, suitable as a support tool for supporting closure of the defect O by the septum primum M2, in the case where the defect O generated at the septum secundum M1 of a heart is usually closed by the septum primum M2, however, further simpler folding is possible as compared with the above embodiment, so as to enhance operability.

The device 3 has, as shown in FIG. 15, the propeller-blade like first member 1 to be indwelled at the left atrial side, and the second member 2 for furnishing pressurization force by the first member 1 onto the septum primum M2, however, any of the both members is configured by the extremely slender elastic wire rod 3.

The first member 1 is configured by four pieces of the propeller-blade shape radial protrusion parts 1a to be enlarged at the right atrial side. The radial protrusion part 1a may have any shape as long as being formed in an arc-shape at least at the tip part, and securing safety; number thereof is not limited to four, and may be further more or less number.

The second member 2 has the joint part 5, which bundles the center part of the radial protrusion parts 1a, or the aligning member 20 jointed to the joint part 5, and the hooking member 30.

The joint part 5 may be any type having elasticity or a non-elastic body as long as being capable of bundling the center part of the radial protrusion parts 1a, however, in the present embodiment, an elastic ring-like wire rod is used.

The aligning member 20 has the both side pieces 21 with V-shaped form, and the center piece 22 protruded from between the both side pieces 21, and each of these pieces 21 and 22 is formed by one slender wire rod. The both side pieces 21 with V-shaped form are jointed to a pair of the radial protrusion parts 1a by hooking at the end part, by which automatic aligning function is fulfilled when the both side pieces 21 elastically connect to the inner surface of opening edge of the defect O.

The hooking member 30 is configured by the bar-like ring body 31 and the elasticity furnishing body 35. The bar-like ring body 31 has the main body 32 formed in a flat and long ellipse or a hairpin shape, by one piece of the extremely slender elastic wire rod 3, and the ring-like part 33 formed by rounding the wire rod at the both ends of the main body 32. At one side of the ring-like part 33, the operating wire 15, which will be described later, is inserted through to be a member for detaching the device D3. In addition, the hooking member 30 is a part to be hooked at the opening edge of the defect O for making the first member 1 in an indwelling state at the left atrial side.

The elasticity furnishing body 35 is jointed to the joint part 5 at the center part, and is configured by one piece of the extremely slender wire rod provided with the loop-like ring connecting parts 36 and 37 at the both ends. Each of the loop-like ring connecting parts 36 and 37 is jointed to the main body 32 of the bar-like ring body 31.

This device D3, as shown in FIG. 16, can be used by delivering, after attaching at the tip of the inner cylinder 12', in a stored state inside the outer cylinder 11', and then extruding from the tip of the inner cylinder 12', however, it can also be used by pushing and delivering the inner cylinder 12' attached with the device D3 at the tip, inside the outer cylinder 11', through the connecting tube 50 or the Y connector 13 provided at the base part of the outer cylinder 11', in an inserted state of only the outer cylinder 11' up to the left atrium, and then extruding from the tip of the outer cylinder 11'. As for this point, explanation will be given later in detail.

The delivery apparatus DL' has the pusher part 41, which has the inner cylinder 12' configured by a dense coil-like spring member provided at the inside of the outer cylinder 11', and the loop-like hooking member 40 provided at the tip part of the inner cylinder 12'; and the operation wire 15 inserted through the inside of the inner cylinder 12' so as to enable forward-backward movement.

The inner cylinder 12' may be any type as long as having flexible configuration in a direction perpendicular to the axis, without forward-backward movement in an axis direction, however, for example, as shown in FIG. 17, it is preferable to use a dense coil-like spring member. Such a dense coil-like spring member generates the space inside, and thus it is also possible to insert the operation wire 15 through this space. It should be noted that, in FIG. 6, the coil-like spring member is shown as a "rough" one for descriptive purposes.

In the present embodiment, as shown in FIG. 17, the sleeve member 44, which is formed with the passage 43 for inserting through the operation wire 15 inside, is fixed at the tip of the inner cylinder 12'. The sleeve member 44 is formed with the flange parts 45 and 46 protruded outward at the tip and the base end side, and between both of the flange parts 45 and 46, the collar member 47 is fitted by insertion so as to enable rotation. The collar member 47 is fixed with the base end of the loop-like hooking member 40 so that the operation wire 15 moves forward and backward through the inside of the loop part 40a of the hooking member 40.

Therefore, when the operation wire 15 is inserted through the loop part 40a of the hooking member 40, the closing device D3 can be retained in the delivery apparatus DL', by inserting through the loop part 40a, after inserting through one of the ring-like part 33 formed at the end part of the bar-like ring body 31; in addition, the closing device D3 can be released from the delivery apparatus DL', by retreating the operation wire 15 from inside the loop part 40a of the hooking member 40.

In particular, by inserting the operation wire 15 through the ring-like part 33 of the closing device D3 inside the loop part 40a of the hooking member 40 in this way, the closing device D3 can be freely rotated around the operation wire 15, and also, because the collar member 47 of the hooking member 40 is provided so as to enable rotation around the sleeve member 44, the closing device D3 makes the operation wire 15 enable rotation around the axis, and thus gives extremely high freedom in attaching the device D3.

The pusher part 41 and the operation wire 15 are, as shown in FIG. 16, jointed by the joint mechanism 48 at the base part side of the outer cylinder 11', and thus in a jointed state, both members move forward and backward together inside the outer cylinder 11', while in a state of unlocking the joint, the operation wire 15 is designed to move forward and backward inside the inner cylinder. As the joint mechanism 48, for example, such a mechanism can be used that an elastic body such as rubber inside or the like is fastened by driving a screw, so that the operating wire 15 and the coil-like spring member are integrated, however, it is not limited thereto and it may be other mechanism.

Next, explanation will be given on action of the present embodiment.

First of all, explanation will be given on the case where the device D3 is delivered in a stored state inside the outer cylinder 11' by being attached at the tip of the inner cylinder 12'. As shown in FIG. 16 and FIG. 17, the device D3 is attached at the tip of the delivery apparatus DL', by inserting the operating wire 15 through the ring-like part 33 of the closing device D3, and then inserting through the loop part 40a of the hooking member 40.

When the pusher part 41 and the inner cylinder 12' are pulled relative to the outer cylinder 11', this pulling force is transmitted from the bar-like ring body 31 to the elasticity furnishing body 35, to the joint part 5 and to the propeller-blade-like radial protrusion parts 1a, and thus the closing device D3 is drawn into the outer cylinder 11'.

Namely, when the closing device D3 is drawn into the outer cylinder 11', the bar-like ring body 31 is drawn into and subsequently the loop-like ring connecting part 37 of the elasticity furnishing body 35 moves along the main body 32 of the bar-like supporting body 31, to take position adjacent to the loop-like ring connecting part 36, and becomes, as shown in FIG. 18, the twofold elasticity furnishing body 35. Four pieces of the radial protrusion parts 1a are drawn by pulling force, and the both side pieces 21 of the aligning member 20 also comes together to the center piece 22, by squeezing around the joint part 5 at the opening edge part of the outer cylinder 11'.

Therefore, the device D3 is stored, as shown in FIG. 19, inside the outer cylinder 11' in a state that the hooking member 30, the joint part 5, the radial protrusion parts 1a and the operating wire 15 are arrayed in almost linearly.

In this state, by insertion of the tip of the outer cylinder 11' up to the left atrium Sl, by the same manner as above, and by extrusion operation of the pusher part 41, as shown in FIG. 20, the first member 1 of the device D3 is extruded from the outer cylinder 11'. By this extrusion, the first member 1 is released from constraint by the outer cylinder 11', and becomes an enlarged state by own elasticity.

Subsequently, when the outer cylinder 11' is retreated a little from inside the left atrium Sl, the first member 1 in an enlarged state pressurizes the septum secundum M1 from the left atrium Sl side of the defect O.

On the other hand, the second member 2 is drawn out from the outer cylinder 11' with retreat movement of the outer cylinder 11'. By this drawing out, the aligning member 20 contacts, as shown in FIG. 21, with the defect O or the opening edge of the communicating passage part of the septum primum M2. Because the aligning member 20 has the V-shaped both side pieces 21, these both side pieces 21 elastically connect to the above-described opening edge, and elastic repulsion force thereof uniformly acts onto the opening edge to fulfill automatic aligning function. In addition, because the center piece 22 of the aligning member 20 is jointed to the jointing part 5 with free inclination and deformation, and also because retreating force for the outer cylinder 11' acts, the first member 1 is concentrically arranged with the defect O, and displacement of the first member 1 can be prevented. Further drawing out results in hooking of the elasticity furnishing body 35 at the opening edge of the right atrium Sr side, and hooking of the hooking member 30 at the opening edge of the right atrium Sr side of the defect, with cooperation of the bar-like ring body 31. In particular, by providing the bar-like ring body 31 at the device D3, the hooking at the right atrium Sr side becomes surer.

As a result, the device D3 results in to surely close the defect O of a heart, because the first member 1 supports closure of the septum primum M2 at the left atrium Sl side, and the hooking member 30 of the second member 2 draws the first member 1.

Finally, by retreating only the operating wire 15 relative to the inner cylinder 12, the operating wire 15 inserted through the ring-like part 33 of the bar-like ring body 31 is unlocked and the device D3 is indwelled.

Then, explanation will be given on the case of delivering by pushing the inner cylinder 12' attached with the device D3 at the tip.

In this case, first of all, the closing device D3 attached at the tip of the inner cylinder 12' is inserted in the connecting tube 50 in advance, to contract and store the closing device D3 inside the connecting tube 50. Then, the tip of the outer cylinder 11' is inserted up to the left atrium Sl, and the connecting tube 50 is connected to the Y connector 13 at the near part of the outer cylinder 11'.

Subsequently, the closing device D3 is delivered inside the outer cylinder 11', in a contracted state, and guided up to the tip of the outer cylinder 11', by further pushing through the inner cylinder 12' along the outer cylinder 11'. Then, the closing device D3 is indwelled by carrying out the same method as in the above-described case.

According to such a use method, it becomes easy to pushing delivery of the device D3, because the inner cylinder 12' is formed by a dense coil-like spring member.

In the present embodiment, the device D3 can be extremely simply handled, because enlargement or storing of the device D3 is carried out by forward-backward movement of the inner cylinder 12' or the operating wire 15. In addition, during the indwelling thereof, the device D3 can be released only by retreating the operating wire 15 from inside the loop of the hooking member 40, which is capable of providing a sure and safe indwelling state, without adding any force to the device D3 or peripheral tissue, and without generation of indwelling displacement, deformation of tissue, unfastening of the device or the like. Furthermore, recover and rearrangement after indwelling is possible by grabbing the bar-like ring body 31 with a general holding-type delivery apparatus.

It is natural that, also in the present embodiment, the membrane-like member 4 of the first embodiment may be provided at the first member 1.

The present invention is not limited to the above-described embodiments, but various modifications are possible by those skilled in the art, within the technical concept of the present invention. For example, the above-described embodiments are those for using in treatment to close a PFO defect, however, the present invention is not limited thereto and may be used also in the case of closing a passage-like defect such as a congenital type of atrial septal defect (ASD), ventricular septal defect (VSD), and patent ductus arteriosus (PDA), by attachment of a membrane body.

In addition, the defect-closure device of the above embodiments is stored simply in a catheter and a hook-like engaging-releasing unit is operated by operation of an operation wire, however, the operation is not limited thereto, and for example, delivery up to the predetermined position by combination with a so-called balloon is also possible; and engaging-releasing may also be one having not only a hook-like structure but also a free unbundling structure.

INDUSTRIAL APPLICABILITY

The present invention can be utilized as a defect-closure device which is capable of surely closing a passage-like defect of PFO, by small area and a simple configuration.

Furthermore, the present application is based on JP application No. 2005-094160 filed on Mar. 29, 2005, whose disclosed content is incorporated by reference in its entirety.

The invention claimed is:

1. A defect-closure device for closing a passage-like defect, in a state that an opening of the passage-like defect in a living body is covered with a septum, comprising:
    a free enlargement-contraction first member comprising elastic wire rods configured to push said septum to said opening and to support the septum in a closed state of the passage-like defect; and
    a free enlargement-contraction second member comprising elastic wire rods and being jointed to said first member via a joint part,
    wherein said second member is jointed to the first member at a base end part of the second member, and an opposing end part of the second member opposite the base end part has a plurality of protrusion parts configured to elastically contact the inner surface of an opening edge of said opening so as to fulfill an automatic aligning function in which the first member is concentrically arranged with the opening of the passage-like defect;
    wherein the joint part is jointed, via an engaging-releasing unit, with an operation wire for pushing the first member and the second member; and
    the engaging-releasing unit is configured to release engagement with the joint part by moving forward and backward relative to the joint part or by rotation of the operation wire relative to the joint part.

2. The defect-closure device according to claim 1, wherein said second member is elastically jointed to said joint part, and has hooking members configured for hooking at the opening edge of the opening of said defect.

3. The defect-closure device according to claim 1, wherein said first member comprises only wire rods.

4. The defect-closure device according to claim 1, wherein said first member is designed so that said wire rods take a coplanar position in an enlarged state.

5. The defect-closure device according to claim 1, wherein said plurality of protrusion parts protrude from said joint part, and the plurality of protrusion parts are positioned apart from each other at a predetermined angle.

6. The defect-closure device according to claim 1, wherein said joint part is designed to have a joint structure so that a base end part of said second member is capable of taking rotational displacement and/or inclination displacement relative to said first member.

7. The defect-closure device according to claim 1, wherein said joint part has length sufficient to make said first member and said second member apart in a predetermined distance.

8. The defect-closure device according to claim 1, wherein said first member and said second member comprise only wire rods.

9. The defect-closure device according to claim 1, wherein the first member comprises a plurality of protruding loops emanating radially outward from a common central region.

10. The defect-closure device according to claim 9, wherein each of the plurality of protruding loops has a propeller-blade shape.

11. The defect-closure device according to claim 9, wherein the second member wraps around the common central region of the plurality of protruding loops.

12. The defect-closure device according to claim 1, wherein the engaging-releasing unit is formed as a folded tip of the operation wire.

13. The defect-closure device according to claim 1, wherein the defect-closure device is configured to be mounted onto a delivery apparatus comprising an inner cylinder through which the operation wire is inserted; a sleeve member fixed at a tip of the inner cylinder; a collar member fitted rotatably against the sleeve member; and a hooking member fixed at one end to the collar member and having a loop part at an opposing end thereof, the loop part for receiving the operation wire on an inside of the loop part; and
    when the operation wire protrudes from the inner cylinder and is received on the inside of the loop part, the operation wire forms an engaging state with the defect-closure device by insertion through a ring-like part of the second member, and the operation wire releases the engaging state when the operation wire is retreated from the inside of the loop part.

14. The defect-closure device according to claim 13, wherein said second member further comprises:
    a plurality of radial protrusion parts, and said joint part bundles said radial protrusion parts at a center part of the second member;
    an aligning member configured by elastic wire rods including two side pieces forming a V-shape, the aligning member configured to elastically contact the inner surface of the opening edge of the opening to fulfill the automatic aligning function, and the aligning member including a center piece protruding between the two side pieces, the center piece being jointed to the joint part; and
    a hooking member configured by elastic wire rods and having a bar-like ring body with a ring part on at least one end of the bar-like ring body, and an elasticity furnishing body which is jointed to the center part of the second member and to the bar-like ring body via loop-like ring connecting parts;
    wherein the bar-like ring body is configured to be provided at the inner surface of the opening edge of the opening.

15. The defect-closure device according to claim 1, wherein the first member comprises a membrane-like member having a membrane body mounted onto the elastic wire rods.

* * * * *